US 9,433,466 B2

(12) United States Patent
Takayama et al.

(10) Patent No.: US 9,433,466 B2
(45) Date of Patent: Sep. 6, 2016

(54) OPTICAL FIBER AND AN UNDERWATER SHOCKWAVE GENERATING DEVICE EMPLOYING THE SAME

(75) Inventors: Kazuyoshi Takayama, Sendai (JP); Hiroaki Yamamoto, Sendai (JP); Hiroaki Shimokawa, Sendai (JP)

(73) Assignee: TOHOKU UNIVERSITY, Miyagi (JP)

( * ) Notice: Subject to any disclaimer, the term of this patent is extended or adjusted under 35 U.S.C. 154(b) by 602 days.

(21) Appl. No.: 13/880,530

(22) PCT Filed: Jul. 27, 2011

(86) PCT No.: PCT/JP2011/067140
§ 371 (c)(1),
(2), (4) Date: Jul. 3, 2013

(87) PCT Pub. No.: WO2012/053267
PCT Pub. Date: Apr. 26, 2012

(65) Prior Publication Data
US 2013/0274726 A1    Oct. 17, 2013

(30) Foreign Application Priority Data
Oct. 19, 2010  (JP) .................... 2010-234858

(51) Int. Cl.
*A61B 18/22*     (2006.01)
*A61B 17/22*     (2006.01)
(Continued)

(52) U.S. Cl.
CPC ......... *A61B 18/22* (2013.01); *A61B 17/22012* (2013.01); *A61B 18/26* (2013.01); *G02B 6/262* (2013.01); *A61B 2017/22024* (2013.01);
(Continued)

(58) Field of Classification Search
CPC .................... A61B 2018/263; G02B 6/262
See application file for complete search history.

(56) References Cited

U.S. PATENT DOCUMENTS

| | | | | |
|---|---|---|---|---|
| 4,273,109 A | * | 6/1981 | Enderby | A61B 18/24 219/121.6 |
| 4,721,357 A | * | 1/1988 | Kovalchick | B24B 19/226 385/139 |

(Continued)

FOREIGN PATENT DOCUMENTS

| | | |
|---|---|---|
| GB | 2291214 A | 1/1996 |
| JP | 50137551 A | 10/1975 |

(Continued)

OTHER PUBLICATIONS

European search report dated May 27, 2014. Application No. EP 11834109.8.

(Continued)

*Primary Examiner* — Daniel Petkovsek
(74) *Attorney, Agent, or Firm* — Browdy and Neimark, PLLC (57) ABSTRACT

An optical fiber is provided which has good laser beam condensation efficiency and is highly resilient, and a shockwave generating device employing same. An optical fiber is employed in an underwater shockwave generating device which projects a laser beam underwater and generates an underwater shockwave. The optical fiber includes a main body part, and a laser convergence part that is disposed upon a leading end thereof. The laser convergence part is configured so as to exhibit an approximately frustum shape wherein the diameter of the leading end is narrower than the diameter of the base end, and such that an interior angle with respect to a radial direction of a lateral face of an axial cross-section gradually decreases toward the front thereof.

9 Claims, 5 Drawing Sheets

(51) Int. Cl.
*G02B 6/26* (2006.01)
*A61B 18/26* (2006.01)

(52) U.S. Cl.
CPC *A61B2017/22025* (2013.01); *A61B 2018/263* (2013.01)

(56) References Cited

U.S. PATENT DOCUMENTS

| | | | | |
|---|---|---|---|---|
| 5,459,803 | A * | 10/1995 | Yamane | G02B 6/245 385/142 |
| 5,928,525 | A * | 7/1999 | Ohtsu | B82Y 20/00 216/11 |
| 5,953,477 | A * | 9/1999 | Wach | A61B 5/14546 385/115 |
| 5,976,175 | A | 11/1999 | Hirano et al. | |
| 6,179,830 | B1 | 1/2001 | Kokubu | |
| 7,356,225 | B2 * | 4/2008 | Loebel | A61B 18/22 385/12 |
| 7,421,186 | B2 * | 9/2008 | Boutoussov | A61B 18/22 385/43 |
| 8,224,138 | B2 * | 7/2012 | Hamada | A61C 1/0046 385/123 |
| 2003/0081899 | A1 * | 5/2003 | Hikichi | G02B 6/4203 385/43 |
| 2003/0165290 | A1 | 9/2003 | Bhagavatula et al. | |

FOREIGN PATENT DOCUMENTS

| | | |
|---|---|---|
| JP | 947518 A | 2/1997 |
| JP | 2001255255 A * | 9/2001 |
| JP | 2004215862 A | 8/2004 |
| JP | 200961083 A | 3/2009 |
| WO | 2008114869 A1 | 9/2009 |

OTHER PUBLICATIONS

Nose, Hidetoshi et al., "Effect of Optical Fiber Output Surface on Laser Induced Shockwave and Its Application", Japanese Journal of APplied Physics, vol. 43, No. 9A, 2004, pp. 6145-6151.

* cited by examiner

OPTICAL FIBER AND AN UNDERWATER SHOCKWAVE GENERATING DEVICE EMPLOYING THE SAME

TECHNICAL FIELD

The present invention relates to an optical fiber and an underwater shockwave generating device employing the same. Specifically, the present invention relates to an optical fiber for irradiating a laser beam underwater to generate the underwater shockwave and an underwater shockwave generating device employing the same.

BACKGROUND ART

Ablation treatment is known as prevalent technology of non pharmacological treatment to the affected area. However, in this treatment, because the treated area is ablated using electrode, it is difficult to treat the deep portion of the arrhythmia of tachyarrhythmia and it has a problem that the serious thrombus obstruction may occurred in combination with the tachyarrhythmia due to the heat generated by the electrode.

Further, the extracorporeal shock wave lithotripsy (ESWL) to crush and remove the stone in the ureter or kidney by instantaneously forming high pressured area in limited space, in which the high pressured area is formed by converging the underwater shockwave generated by irradiating the pulse laser beam underwater, is established.

The applicant has succeeded in providing the small underwater shockwave generating device incorporating above underwater shockwave converging method, which can be employed in the catheter, like shown in patent document 1.

Further, it is known that the strong shockwave can be generated by using the optical fiber having a rough surface rather than using the optical fiber having a mirror surface, like shown in paragraph 3.6 of non patent document 1.

PRIOR ART DOCUMENTS

Patent Document

Patent Document 1: Japanese published Patent Document 2009-61083

Non Patent Document

Non Patent Document 1: H. Nose et al., Effect of Optical Fiber Output Surface on Laser Induced Shock Wave and Its Application, Japanese Journal of Applied Physics Vol. 43, No. 9A, 2004, pp. 6145-6151

SUMMARY OF THE INVENTION

Problems to be Resolved by the Invention

An underwater shockwave generating device of Patent Document 1 resolved the problem of treating the deep portion of affected area and problem of preventing the thrombus obstruction due to the heat generated near the affected area. However, it was known that it lacks the durability. Especially, the water penetrate inside from the fine cracks formed during the shape forming and, when the laser beam is irradiated, the destruction begins from this fine cracks. Therefore, it is known that the strength of the shockwave dramatically decrease after the first irradiation or a few irradiation due to the wreck formed on the leading end of the optical fiber. Hence, the improvement of the durability of the optical fiber is necessary to construct the good underwater shockwave generating device.

The present invention is directed to provide an optical fiber for an underwater shockwave generating device and an underwater shockwave generating device employing the same, which can generate shockwave having large energy and have high durability.

Means of Solving the Problem

The optical fiber of the present invention is an optical fiber for an underwater shockwave generating device in which the underwater shockwave is generated by irradiating the laser beam underwater. It is characterized in that the optical fiber has a linear main body part and a laser beam convergence part disposed on a front end thereof; where the laser beam convergence part is a solid of revolution having an axis where a radius gradually decreases toward a front, the laser beam convergence part has a truncated cone shape where a leading end has a planar surface perpendicular to the axis, an interior angle with respect to a radial direction of a lateral side of an axial cross-section (longitudinal sectional view) of the laser beam convergence part gradually decreases toward the front, and the outer surface of the laser beam convergence part is configured to be a mirror surface.

In the optical fiber of above, it is preferable that the lateral side of an axial cross-section of the laser beam convergence part is formed of plural of a straight segments (or straight lines), or the lateral side of an axial cross-section of the laser beam convergence part is formed of curved segment (or curved line), or the lateral side of an axial cross-section of the laser beam convergence part is formed of combination of straight and curved segments.

The underwater shockwave generating device of this invention comprises the optical fiber of the present invention, a columned shape reflector having a concave surface at a front end, a blocking membrane closing an opening of the concave surface, and a liquid charged between the concave surface and the blocking membrane. The reflector has the concave surface of an ellipsoid of revolution shape in which a major axis is a rotating axis, and a centered hole to insert the optical fiber for the optical fiber to communicate with the concave surface is formed on the major axis. The optical fiber is fixed to the reflector so as a front end of the laser beam convergence part is located on a focal point of the concave surface.

Effect of the Invention

The optical fiber of the present invention has a linear main body part and a laser beam convergence part disposed on a front end thereof; and the laser beam convergence part is a solid of revolution having an axis where a radius gradually decreases toward a front, therefore the laser beam irradiated from the base of the optical fiber is concentrated at the leading end of the optical fiber and a strong shockwave can be generated efficiently to the pinpoint. Especially, because an interior angle with respect to a radius direction of a lateral side of an axial cross-section of the laser beam convergence part gradually decreases toward the front, the laser beam can be converged according to the ray tracing algorithm. Further, because the laser beam convergence part has a truncated cone shape where a leading end has a planar surface perpendicular to the axis, high durability can be obtained.

In such an optical fiber, when the outer surface of the laser beam convergence part is configured to be a mirror surface, the formation of the fine cracks on the outer surface can be prevented, and the durability can be further enhanced. Moreover, the diffuse reflection on the inner surface of the laser beam convergence part can be prevented and raise the energy density of the laser beam converged and headed to the front end. Especially, because the laser beam convergence part has approximately truncated cone shape where the radial decrease toward the front end, the generated shockwave will be stronger than the optical fiber made of conventional method, and the higher durability can be obtained, although the mechanical strength of optical fiber having approximately truncated cone is smaller than optical fiber having the cylinder end.

In such an optical fiber, when the lateral side of an axial cross-section of the laser beam convergence part is formed of plural of a straight segments, or when the lateral side of an axial cross-section of the laser beam convergence part is formed of curved segment, or when the lateral side of an axial cross-section of the laser beam convergence part is formed of combination of straight and curved segments, the laser beam can be converged according to the ray tracing algorithm, and the shockwave can be generated stably.

The underwater shockwave generating device of the present invention has the optical fiber of the present invention, so that the durability of the optical fiber is high and the durability of the device as a whole will be high. Further, because it is designed so as the laser beam converge to the front end of the optical fiber, the generated shockwave will converge accurately to the exterior focal point of the reflector and the energy efficiency will be high. Moreover, the large shockwave can be generated farther away from the device. Therefore, it can be used for advanced treatment.

BRIEF DESCRIPTION OF THE DRAWING

FIG. FIG. 3a is diagrammatic illustration of mathematical formula of the laser beam convergence part of FIG. 2a, FIG. 3b is a diagrammatic illustration of laser beam which is irradiated from the laser beam convergence part of the optical fiber of FIG. 2a.

FIG. 4 A side cross sectional view showing the reflector of FIG. 1a.

EMBODIMENT FOR CARRYING OUT THE INVENTION

Hereinafter, an underwater shockwave generating device of present invention is described using FIG. 1.

The underwater shockwave generating device 10 is composed of the optical fiber 11, the reflector 12 fixing the optical fiber, the blocking membrane 13 closing the opening of the concave surface formed on the front end of the reflector 12, the liquid 14 charged with in the space between the concave surface and the blocking membrane. This underwater shockwave generating device 10 is a small device which is fixed to the front end of the catheter 15.

The optical fiber 11 is made of quartz and the dehydroxylation treatment is conducted. The optical fiber 11 comprises the linear main body part 16 and a laser beam convergence part 17 disposed on a front end thereof. The main body part 16 having a diameter of 0.1 to 1.0 mm, preferably 0.5 to 0.7 mm, and especially 0.6 mm is used.

The laser beam convergence part 17 is configured to be approximate small truncated cone of a solid revolution where the shape is formed by rotating around the axis of main body part. The radius of the shape gradually decreases toward the front, and the leading end is formed to be the planar surface 18a perpendicular to the axis of the main body part. The ratio of diameter of the front end of the laser beam convergence part 17 to diameter of the base end of the laser beam convergence part is 1/1.5 to 1/6, preferably 1/2 to 1/3, especially, 1/2.

The interior angle θ with respect to the radial direction of the lateral side of the axial cross-section of the laser beam convergence part is configured to gradually decrease toward the front side (front) from the base side. Further, considering the durability of the laser beam convergence part, it is preferable to have the height of the laser beam convergence part to be lower than the diameter of the optical fiber.

The outer surface of the laser beam convergence part 17 is configured to be mirror surface, and no fine cracks and asperity is formed on the outer surface. Therefore, it prevents the destruction of the laser beam convergence part 17 originated from the crack due to the penetration of the water from the fine crack and asperity.

The optical lens formation method can be used for the mirror finish of the laser beam convergence part 17. Especially, method to use the designated tools for optical lens, and to prepare several polisher of 24 micron to 1 micron, and to polish the object with the polisher in order from the rough one can be cited.

FIGS. 2a to 2e can be cited for the shape of the truncated cone of the laser beam convergence part 17.

Figure 2:
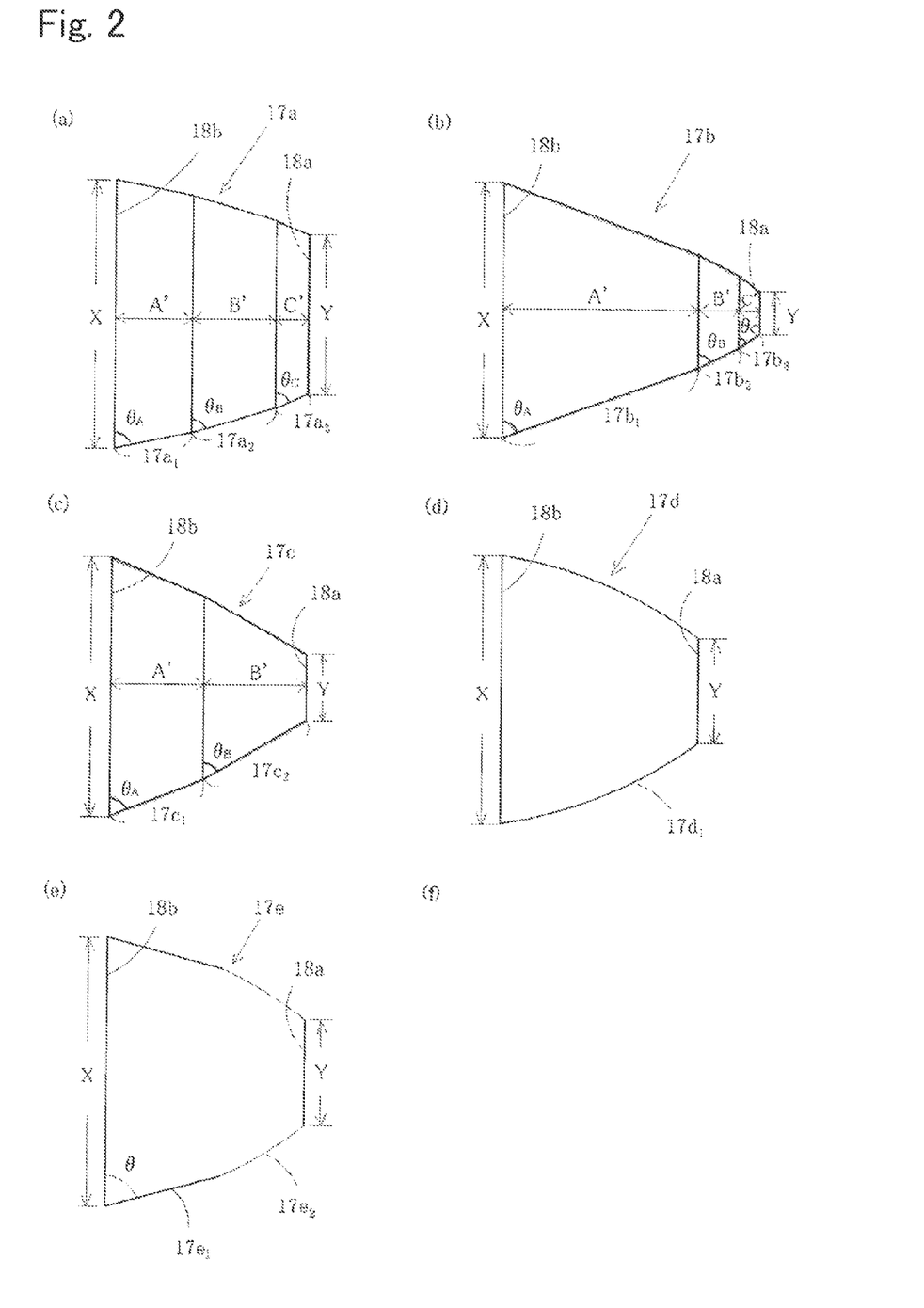
FIG. 2a to FIG. 2e are respectively an external shape of the laser beam convergence part of the optical fiber of the present invention.

The laser beam convergence part 17a of FIG. 2a has the shape that the diameter Y of the leading end 18a is approximately half the size of the diameter X of the base end 18b, and that the axial cross-section is approximately trapezoid. The side of the trapezoid is formed of three straight segments (or lines) ($17a_1$, $17a_2$, $17a_3$), where the interior angles ($\theta_A$, $\theta_B$, $\theta_C$) with respect to base line of the trapezoid (a radial direction of a truncated cone) decrease gradually from the base side (main body part, left side of the figure) ($\theta_A > \theta_B > \theta_C$).

In the laser beam convergence part 17a of FIG. 2a, the side of the trapezoid which is an axial cross-section of the lateral surface formed of three straight segments was cited. However, if it satisfies the equation of below, the side may be configured with 2 straight segments (or lines), or 4 or more straight segments (or lines). Determining the interior angles ($\theta_1$, $\theta_2$, $\theta_{n-1}$, $\theta_n$) of each straight line respect to radial direction from the base end to the front end.

$$0.4 < \tan(2\theta_n - \tfrac{1}{2}\pi)/\tan \theta_n < 0.5$$

$$2\theta_n - \tfrac{1}{2}\pi < \theta_{n+1} < \theta_n, \; n=1,2,3 \ldots$$

except: $\tfrac{1}{4}\pi < \theta_n < \tfrac{1}{2}\pi$ \hfill (formula 1)

Figure 3:
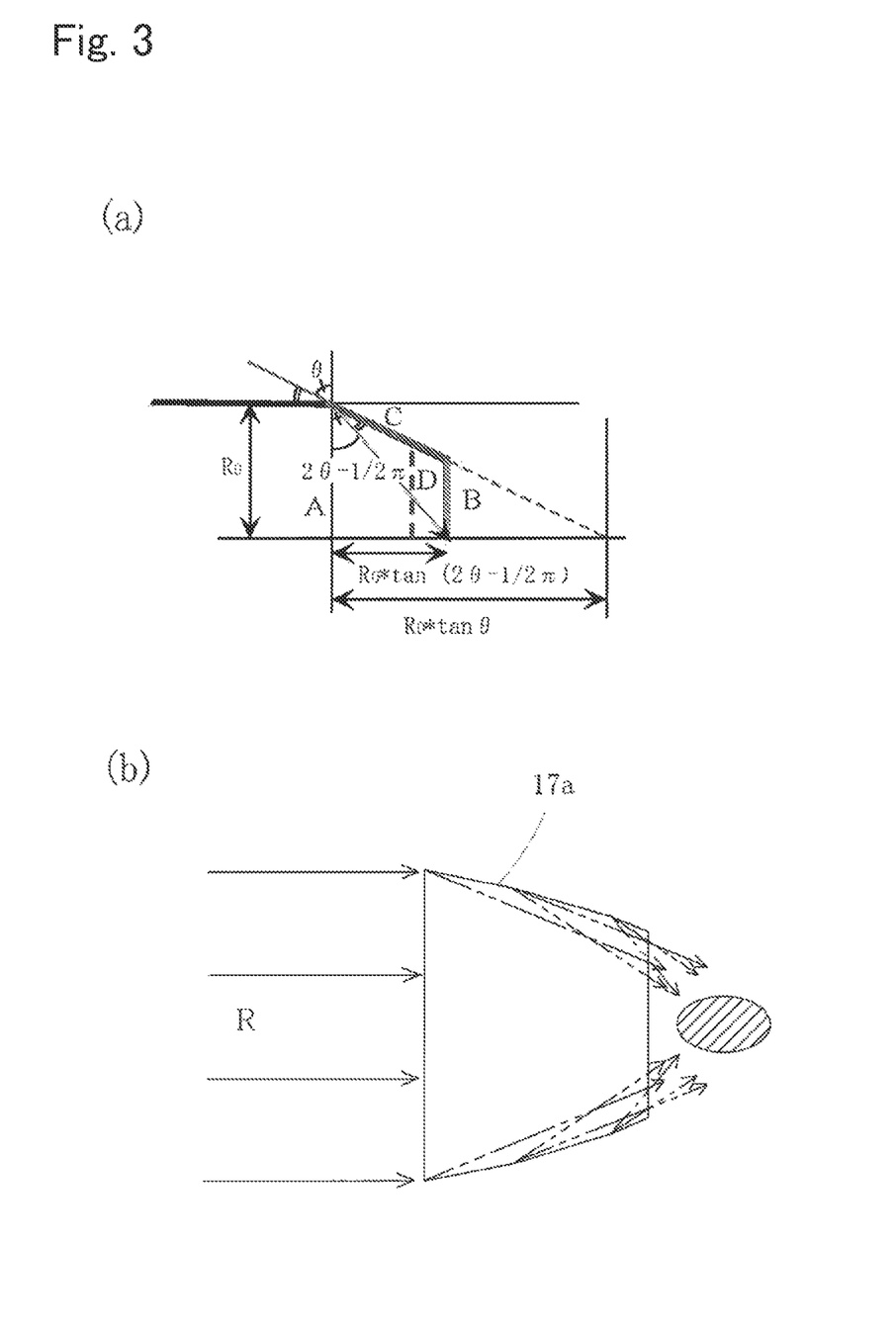

Like seen in FIG. 3a, the laser beam which reflects the interior surface of line C having interior angel of θ n respect to radial direction passes through the flat surface D arranged between the face A and face B which is formed by the base end of the line and front end of the line respectively. Therefore, the laser beam can be focused efficiently, and strong shockwave can be generated. Further, considering the durability of the laser beam convergence part, the height of the truncated cone is preferable to be smaller than the diameter of the optical fiber.

The laser beam convergence part 17b of FIG. 2b has the shape that the diameter Y of the leading end 18a is approximately ⅙ of the size of the diameter X of the base end 18b, and the side of the trapezoid is formed of three straight segments ($17b_1$, $17b_2$, $17b_3$). The height (A'+B'+C') of the laser beam convergence part 17b is made to be same as diameter X of the base end 18b. The interior angles ($\theta_A$, $\theta_B$, $\theta_C$) with respect to base line of the trapezoid (a radial direction of a truncated cone) decrease gradually from the base side (main body part, left side of the figure) ($\theta_A > \theta_B > \theta_C$).

The laser beam convergence part 17c of FIG. 2c has the shape that the diameter Y of the leading end 18a is approximately ⅓ of the size of the diameter X of the base end 18b. The side of the trapezoid is formed of two straight segments ($17c_1$, $17c_2$). The interior angles ($\theta_A$, $\theta_B$) with respect to base line of the trapezoid (a radial direction of a truncated cone) decrease gradually from the base side (main body part, left side of the figure) ($\theta_A > \theta_B$).

In this embodiment, the interior angle $\theta_A$ of the segment 17c1 is set at around the optimum angle. That is according to the definition of the optimum angel (optimum angle $\theta c = \arcsin(n2/n1)$, n1: refractive index of optical fiber, n2: refractive index of water), when the laser beam which passes through the segment 17c1 and vanishes after transmitting into the water, the theoretical optimum angle would be 67.84, considering that the refractive index of the water is 1.329 and the refractive index of the optical fiber is 1.435. Further, considering the durability of the laser beam convergence part, the height of the approximate truncated cone is preferable to be smaller than the diameter of the optical fiber and therefore interior angle θA is preferable to be smaller than 76.8 degree. As a result, $\theta_A$ would be $67.84 < \theta_A < 76.8$.

The laser beam convergence part 17d of FIG. 2d has the shape that the diameter Y of the leading end 18a is approximately half the size of the diameter X of the base end 18b. The side 17d1 of the trapezoid is formed of curved segment (or line) protruding outside. However, the side 17d1 may be formed of two or more curvatures.

The laser beam convergence part 17e of FIG. 2e has the shape that the diameter Y of the leading end 18a is approximately half the size of the diameter X of the base end 18b. The side 17d1 of the trapezoid is formed of one straight segment 17ea and one curved segment 17e2.

The laser beam convergence part 17a to 17e of FIGS. 2a to 2e has a shape of approximately truncated cone having the diameter Y of the front end 18a be smaller than the diameter X of the base end 18b, and the interior angle respect to a radial direction of a lateral side of an axial cross-section of the laser beam convergence part continuously or non continuously and gradually decreases toward the front. Therefore, the effect of the present invention, which is that the efficiency of the focusing of the laser beam can be enhanced and the durability of the laser beam convergence part 17 of the optical fiber can be obtained.

Since the optical fiber 17 is configured as above, the laser beam converges according to the ray tracing algorithm, when the laser beam R is irradiated to the laser beam convergence part 17a of FIG. 2a, like shown in FIG. 3b.

Figure 4:
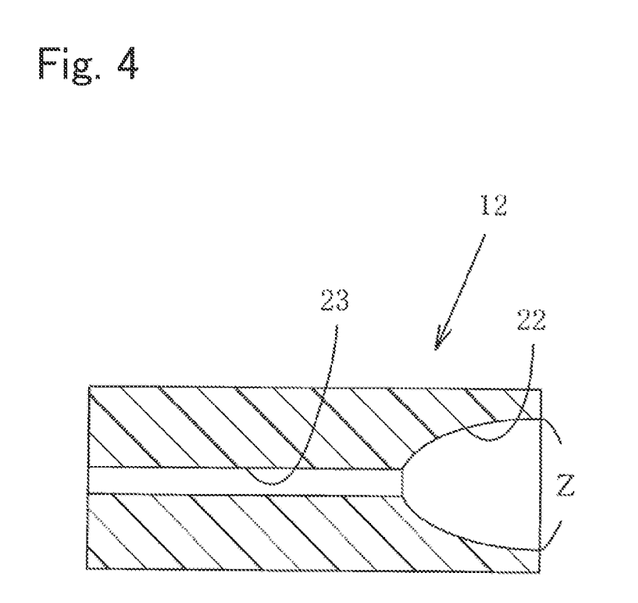

The reflector 12 has column shape configuration and comprises the concave surface 22 of spheroidal where the long axis is rotation axis, and the center hole 23 which is formed on the rotation axis and which let the optical fiber 11 through to communicate with the concave surface. The length of the minor axis (diameter Z of the opening) of concave surface 22 is to be 2.0 to 2.5 mm, preferably to be 2.3 mm. The length of the major axis of the concave surface 22 can be determined according to the depth of the affected area, but it is preferable to have the ratio of major axis to minor axis to be 1.2 to 1.6, preferable to be 1.4 to 1.45.

Figure 1:
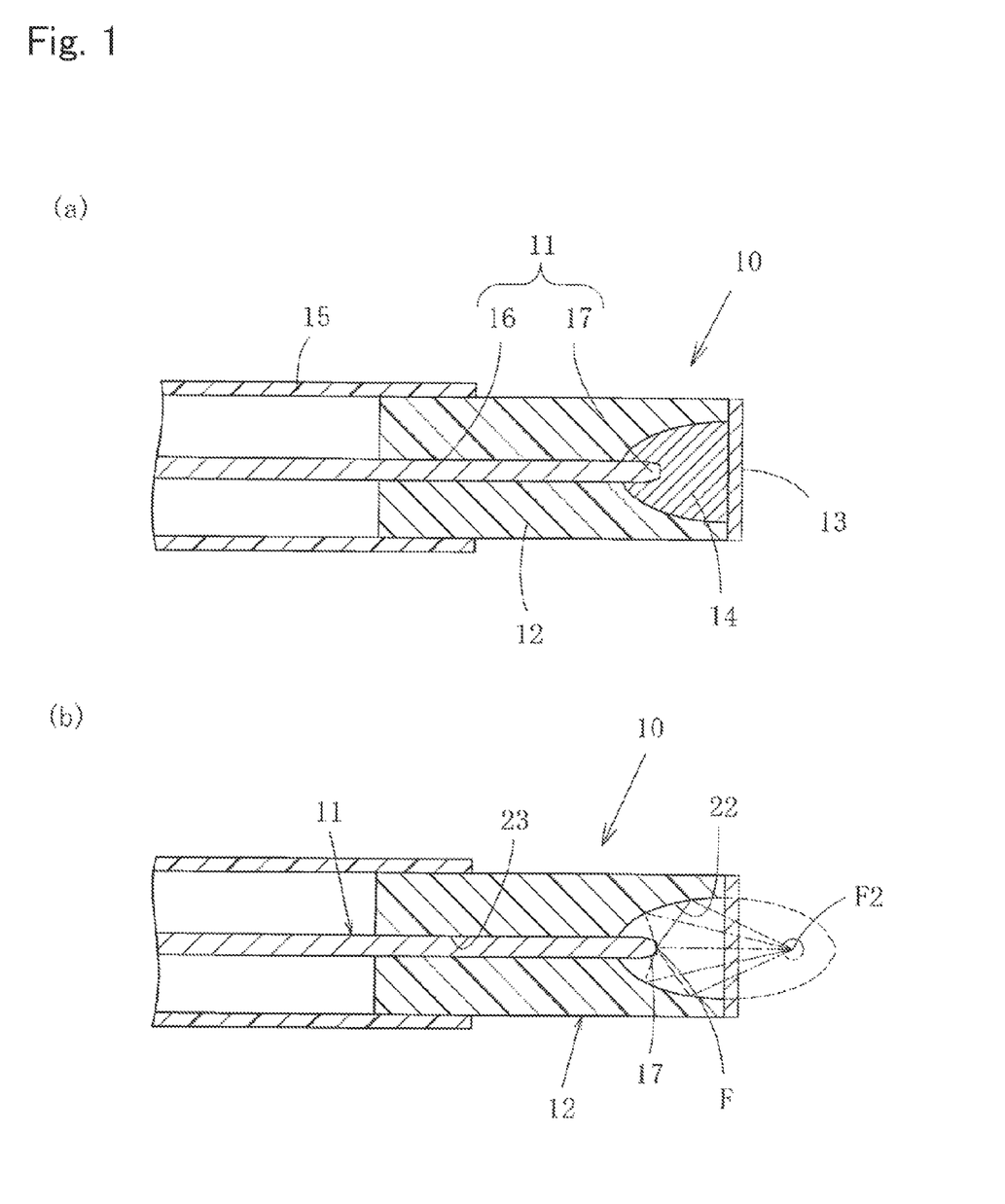
FIG. 1a is a side cross sectional view showing one embodiment of the underwater shockwave generating device of the present invention.
FIG. 1b is reflection scheme of the shockwave generated from the device.

The blocking membrane 13 of FIG. 1 is a thin film made of plastic and has elasticity. For such a material, polyethylene can be cited.

As for the liquid 14, water, saline solution and etc. can be cited.

The catheter 15 has a flexibility, and plastic material such as polyurethane, polyamide, elastomers which has similar character, and silicon rubber, can be used.

The underwater shockwave generating device 10 is manufactured by arranging the leading end 18a of the laser beam convergence part 17 of the optical fiber 11 on one of the focal point of the concave surface 22 of the reflector and by fixing the optical fiber 11 inserting through the center hole 23 of the reflector 12 (see FIG. 1b). So, the laser beam irradiated from the optical fiber 11 generates the shockwave at the focal point F1. The shockwave generated on the focal point F1 is than diffused in 360 degree, and convergence to the outer focal point F2 of the reflector after reflected from the concave surface of the reflector 12. The underwater shockwave generating device 10 of the present invention can converge the shockwave at the predetermined distance from the front end. Therefore, for example, the treatment of deep portion of the tachyarrhythmia source can be conducted accurately and safely. Especially, because the laser beam convergence part 17 of the optical fiber 11 has high durability which does not form any scratches even after using plural times, and which can create the large shockwave from small energy.

The laser beam of which the pulse width of 50 to 120 nano second, preferably 70 to 100 nano second, especially 70 nano second, and energy per one pulse of 30 to 50 mJ can be used for the underwater shockwave generating device of the present invention. For such a laser, Ho:YAG laser of Q switch is preferable.

EXAMPLE

The leading end of the optical fiber is fabricated as below.

Example 1

The laser beam convergence part 17a of FIG. 2a was prepared (example 1). The diameter X of the base end 18b is 0.6 mm, and the diameter Y of leading end 18a is 0.344 mm. The angle of the three straight segments ($17a_1$, $17a_2$, $17a_3$) configuring the lateral side of an axial cross-section are 78.9 degrees, 73.4 degrees, and 65.6 degrees respectively. The height (A', B', C') are 0.175 mm, 0.186 mm, 0.072 mm respectively.

The outer surface of the laser beam convergence part 17a was polished and mirrored by using the abrading agent in order from fused alumina of 24 micron, 16 micron, 10 micron to oxidized cerium of 1 micron, and using the tools for preparing optical lens.

Example 2

The laser beam convergence part 17b of FIG. 2b was prepared (example 2). The diameter X of the base end 18b is 0.6 mm, and the diameter Y of leading end 18a is 0.106 mm. The angle of the three straight segments ($17b_1$, $17b_2$, $17b_3$) configuring the lateral side of an axial cross-section are 70 degrees, 61 degrees, and 55 degrees respectively. The height (A', B', C') are 0.457 mm, 0.060 mm, 0.083 mm respectively.

Example 3

The laser beam convergence part 17c of FIG. 2c was prepared (example 3). The diameter X of the base end 18b is 0.6 mm, and the diameter Y of leading end 18a is 0.148 mm. The angle of the two straight lines ($17c_1$, $17c_2$) configuring the lateral side of an axial cross-section are 69 degrees, and 60 degrees respectively. The height (A', B') are 0.175 mm, 0.213 mm, 0.242 mm respectively.

Example 4

The optical fiber 11 having the laser beam convergence part 17a of example 1 and the reflector 12 having the concave fave of severed ellipsoid shape where the diameter of the minor axis is 4 mm, was prepared. The purified water (liquid 14) was filled in the concave face 22 of the reflector and the closing membrane 13 of silicon rubber having the thickness of 0.1 mm was fixed and sealed on the opening end of the reflector (example 4). The optical fiber 11 was fixed so that the leading end of the laser beam convergence part 17a is aligned with the first focal point of the reflector (F1 of the FIG. 1b).

Comparative Example 1

The conventional optical fiber having the tubular leading end in which cleavage treatment has been conducted, is prepared. And the underwater shockwave generating device of comparative example 1 is manufactured using the reflector 12 of example 1, blocking membrane 13, and liquid 14. The front end of the optical fiber is fixed on the first focal point of the reflector.

Comparative Example 2

The optical fiber having the laser beam convergence part of truncated cone in which the diameter of the base end is 0.6 mm, diameter Y of the leading end is 0.35 mm, and the height Z is 0.43, is prepared. The outer surface of the laser beam convergence part is treated with the sandpaper of number 4000 (rough face). And the underwater shockwave generating device of comparative example 2 is manufactured using the reflector 12 of example 1, blocking membrane 13, and liquid 14. The front end of the optical fiber is fixed on the first focal point of the reflector.

Comparative Example 3

The optical fiber having the laser beam convergence part of non spherical shape (bullet shape) in which the lateral side of an axial cross-section is to be curved toward the front end and the front end is formed to be round and the diameter of the base end is 0.6 mm, is prepared. The outer surface of the laser beam convergence part is treated with the sandpaper of number 4000 (rough face). The underwater shockwave generating device of comparative example 3 is manufactured using the reflector 12 of example 1, blocking membrane 13, and liquid 14. The front end of the optical fiber is fixed on the first focal point of the reflector.

Figure 5:
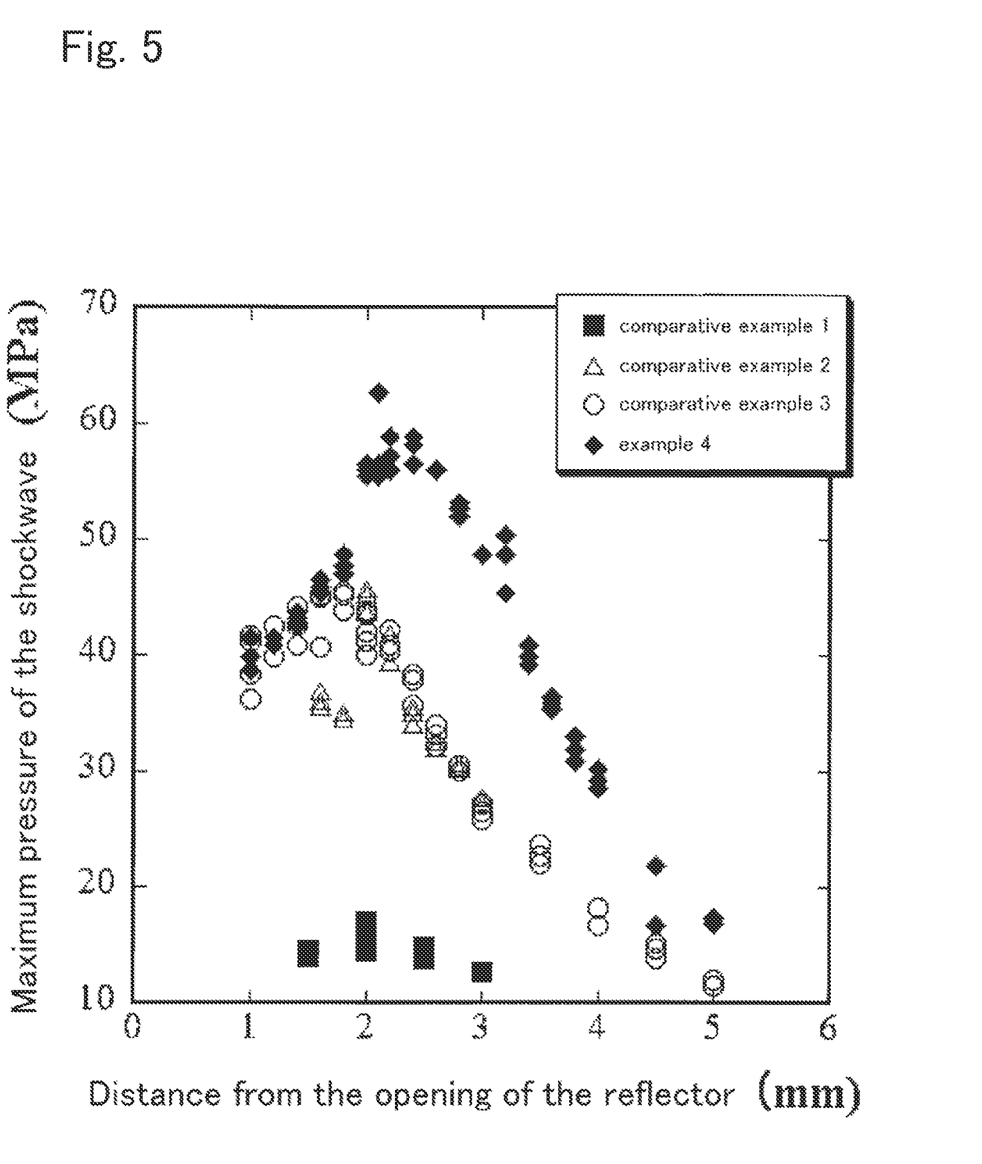
FIG. 5 A graph showing the relationship between the distance from the device and the strength of the shockwave generated from the underwater shockwave generating device.

Ho:YAG laser (oscillation cycle of 3 Hz, the energy of the laser output is 35 mJ/pulse) was irradiated to the underwater shockwave generating device of example 4, comparative example of 1 to 3 and the shockwave was generated. The difference of largest excess pressure to the distance of the front end of the device is shown in FIG. 5.

When the device of example 4 is used, the shockwave of 55 to 65 MPa (converging wave) were observed.

However, when the device of comparative example 1 is used, only the shockwave of 35 to 45 MPa (converging wave) were observed.

Further, in example 4, the maximum was observed at 2 mm or more from the front end of the device. On the other hand, in comparative example 1 to 3, the maximum was observed at 2 mm or less from the front end of the device.

As for the durability, the optical fiber of the comparative example 2 was damaged after continuous irradiation of 300 seconds and the optical fiber of the comparative example 3 was damaged after the continuous irradiation of 5 seconds. Whereas the optical fiber of example 4 did not observe any damages after the 80 times of irradiation.

DESCRIPTION OF THE NUMERAL 10 underwater shockwave generating device.
11 optical fiber
12 reflector
13 blocking membrane
14 liquid
16 main body part
17 laser beam convergence part
17a to 17e laser beam convergence part
17a1 to 17a3, 17b1 to 17b3, 17c1, 17c3 lateral side
18a leading end
18b base end
22 concave surface
23 center hole

The invention claimed is:

1. An optical fiber for use in an underwater shockwave generating device that generates an underwater shockwave by irradiating a laser beam underwater, said optical fiber comprising;
  a linear main body part and a laser beam convergence part disposed on a front end thereof,
  wherein the laser beam convergence part has a central longitudinal axis and a radius extending from the central longitudinal axis to an outer circumference of the laser beam convergence part gradually decreases toward a front end of the laser beam convergence part,
  wherein the laser beam convergence part has an approximate solid truncated cone shape where a leading end has a planar surface perpendicular to the axis,
  wherein an interior angle with respect to a radial direction of a lateral face of an axial cross-section of the laser beam convergence part continuously or non-continuously and gradually decreases toward the front, and
  wherein an outer surface of the laser beam convergence part is configured to be a mirror surface by mirror finishing.

2. An optical fiber according to claim 1, wherein the lateral side of an axial cross-section of the laser beam convergence part is formed of a plurality of straight segments.

3. An optical fiber according to claim 1, wherein the lateral side of an axial cross-section of the laser beam convergence part has a curved segment shape.

4. An optical fiber according to claim 1, wherein the lateral side of an axial cross-section of the laser beam convergence part is formed of a combination of straight and curved segments.

5. An underwater shockwave generating device, comprising;
the optical fiber of claim 1,
a reflector having concave surface at a front end,
a blocking membrane closing an opening of the concave surface,
a liquid charged between the concave surface and the blocking membrane,
wherein the reflector has the concave surface of an ellipsoid of revolution shape in which a major axis is a rotating axis, and a centered hole for the optical fiber to communicate with the concave surface formed on the major axis,
wherein the optical fiber is fixed to the reflector so as a front end of the laser beam convergence part is located on a focal point of the concave surface.

6. An underwater shockwave generating device according to claim 5, wherein a length of the laser beam convergence part is the same as or shorter than a diameter of the optical fiber.

7. An optical fiber according to claim 1, wherein said underwater shockwave generating device further comprises a reflector having a concave surface at a front end; wherein said membrane closes the front end of the concave, and wherein said liquid is charged in the concave surface.

8. An optical fiber according to claim 1, wherein a length of the laser beam convergence part is the same as or shorter than a diameter of the optical fiber.

9. An underwater shockwave generating device, comprising;
an optical fiber,
a reflector having a concave surface at a front end,
a blocking membrane closing an opening of the concave surface,
a liquid charged between the concave surface and the blocking membrane,
wherein the reflector has the concave surface of an ellipsoid of revolution shape in which a major axis is a rotating axis, and a centered hole for the optical fiber to communicate with the concave surface formed on the major axis,
wherein the optical fiber comprises a linear main body part and a laser beam convergence part disposed on a front end thereof,
wherein the optical fiber is fixed to the reflector so as a front end of the laser beam convergence part is located on a focal point of the concave surface,
wherein an interior angle with respect to a radial direction of a lateral face of an axial cross-section of the laser beam convergence part continuously or non-continuously and gradually decreases toward the front, and
wherein an outer surface of the laser beam convergence part is configured to be a mirror surface by mirror finishing.

* * * * *